(12) United States Patent
Bilotti et al.

(10) Patent No.: US 7,810,690 B2
(45) Date of Patent: Oct. 12, 2010

(54) SURGICAL STAPLING INSTRUMENT

(75) Inventors: Federico Bilotti, Via Padre G.A. Filippini (IT); Michele D'Arcangelo, Via Benedetto Croce (IT); Antonio Longo, Via Maqueda (IT); Jesse J. Kuhns, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 358 days.

(21) Appl. No.: 11/662,105

(22) PCT Filed: Oct. 9, 2004

(86) PCT No.: PCT/EP2004/010138

§ 371 (c)(1),
(2), (4) Date: Jul. 9, 2007

(87) PCT Pub. No.: WO2006/027014

PCT Pub. Date: Mar. 16, 2006

(65) Prior Publication Data

US 2009/0236399 A1    Sep. 24, 2009

(51) Int. Cl.
A61B 17/064    (2006.01)
A61B 17/03     (2006.01)

(52) U.S. Cl. .................. 227/175.1; 227/176.1; 606/219

(58) Field of Classification Search ... 227/175.1–182.1; 606/219, 131, 151
See application file for complete search history.

(56) References Cited

U.S. PATENT DOCUMENTS 4,728,020 A * 3/1988 Green et al. ................... 227/19
5,395,030 A * 3/1995 Kuramoto et al. ......... 227/179.1
5,605,272 A * 2/1997 Witt et al. ................. 227/175.2
5,762,255 A * 6/1998 Chrisman et al. ......... 227/175.2
5,762,256 A * 6/1998 Mastri et al. .............. 227/176.1
5,779,132 A * 7/1998 Knodel et al. ............. 227/176.1
5,797,536 A * 8/1998 Smith et al. ............... 227/175.1
5,807,393 A * 9/1998 Williamson et al. ........... 606/32
6,443,973 B1 * 9/2002 Whitman .................... 606/219
6,669,073 B2 * 12/2003 Milliman et al. ......... 227/175.2
6,695,199 B2 * 2/2004 Whitman .................. 227/180.1
6,716,233 B1 * 4/2004 Whitman .................... 606/219
6,805,273 B2 * 10/2004 Bilotti et al. .............. 227/180.1
7,111,769 B2 * 9/2006 Wales et al. ............... 227/178.1
7,210,609 B2 * 5/2007 Leiboff et al. ............. 227/180.1
7,434,717 B2 * 10/2008 Shelton et al. ............ 227/176.1
7,506,791 B2 * 3/2009 Omaits et al. ............. 227/177.1
7,575,144 B2 * 8/2009 Ortiz et al. ................ 227/175.1
2004/0084505 A1 * 5/2004 Bilotti et al. .............. 227/180.1
2004/0134964 A1 * 7/2004 Adams et al. ............. 227/176.1

FOREIGN PATENT DOCUMENTS

WO    WO 01/91646 A1    12/2001

* cited by examiner

*Primary Examiner*—Paul R Durand

(57) ABSTRACT

A surgical stapling instrument including a staple fastening assembly with a curved cartridge device and a curved anvil. The cartridge device has at least one curved open row of staples which are formed by a staple forming face of the anvil (12). The anvil can be moved relatively with respect to the cartridge device (10) the device further includes a handle in the proximal end region of the instrument and is operatively connected to the staple fastening assembly. A flexible backbone, preferably an endoscope, is arranged between the handle and the staple fastening assembly and guides force transmitters of the moving device and the staple driving device.

17 Claims, 13 Drawing Sheets

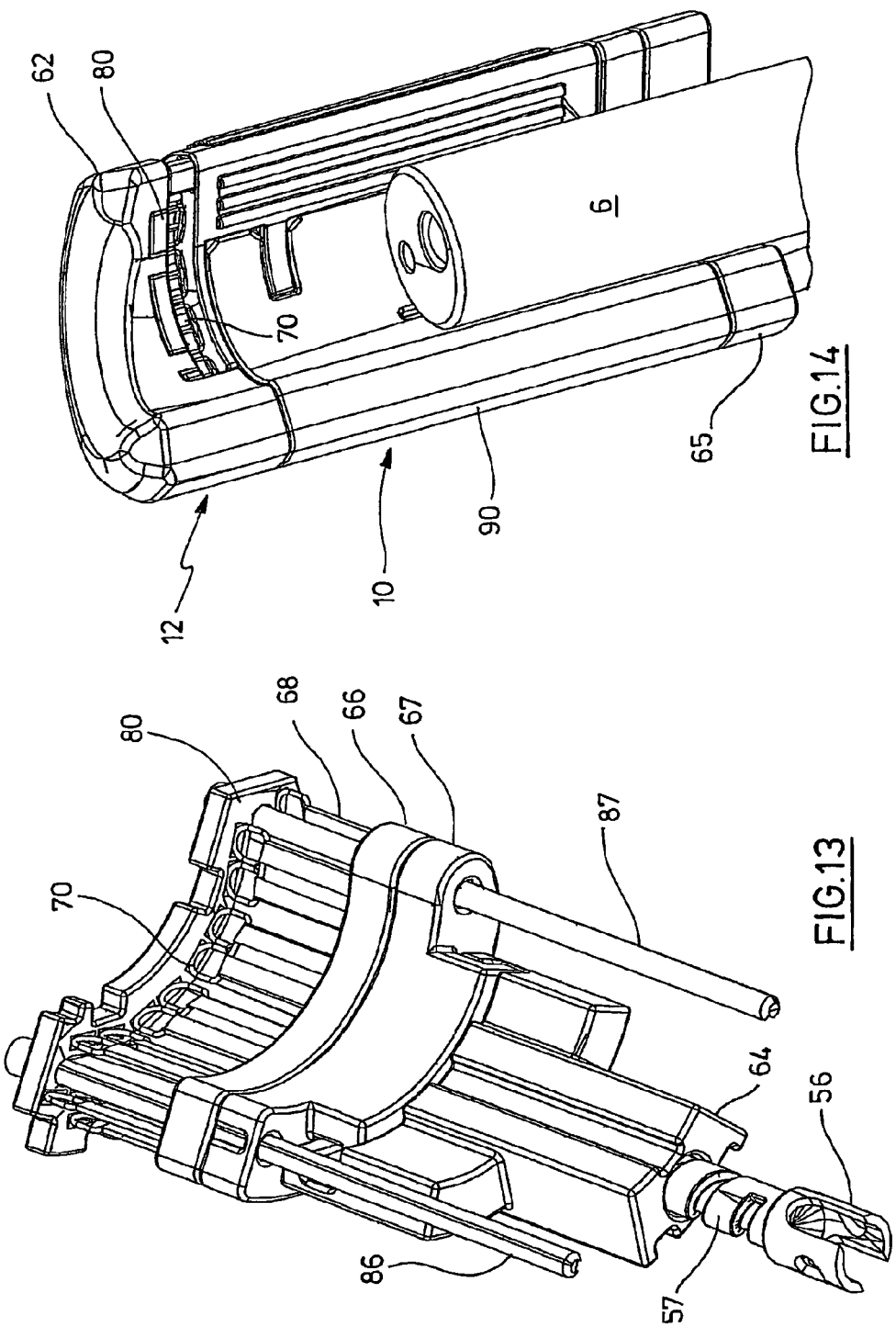

SURGICAL STAPLING INSTRUMENT

FIELD

The invention relates to a surgical stapling instrument, which can be used, e.g., in the diagnosis and/or therapy of pathologies of the lower gastrointestinal tract.

BACKGROUND

Such a surgical stapling instrument is known from WO 01/91646 A1. WO 01/91646 A1 discloses a surgical stapling instrument having a staple fastening assembly located in the distal end region of the stapling instrument, a rigid shaft, and a handle extending from the shaft in the proximal end region of the stapling instrument. The staple fastening assembly includes a curved cartridge device, which comprises several curved open rows of staples having a concave side and a convex side. A curved anvil is arranged opposite to the cartridge device. The anvil has a staple forming face and is adapted to cooperate with the cartridge device for forming the ends of the staples exiting from the cartridge device. The anvil can be moved relatively with respect to the cartridge device from a spaced position for positioning tissue therebetween to a closed position for clamping the tissue. Moreover, a knife is contained in the cartridge device and is positioned on the concave side of at least one row of staples and optionally the convex side of at least one row of staples.

SUMMARY

The surgical stapling instrument disclosed in WO 01/91646 A1 can be used to excise tissue, e.g. polyps, and to stop bleeding virtually immediately. In a surgical procedure, the stapling instrument is introduced, e.g., into the anal canal and moved to the site of the tissue to be resected. The tissue to be excised can be pulled into the area between the anvil and the cartridge device, when the cartridge device and the anvil are in a spaced or open position, by means of a separate tissue grasping instrument. Afterwards, the anvil is moved relatively with respect to the cartridge device in order to clamp the tissue. When the cartridge device and the anvil have reached the closed position, the surgeon can "fire" the instrument, which means that the staples are driven out of the cartridge device, penetrate the tissue, whereupon the ends are bent by the anvil, and the knife is moved towards the anvil in order to cut the tissue. When the instrument is opened, the completely excised tissue can be safely removed from the patient's body together with or prior to removing the instrument itself.

A particular advantage of the surgical stapling instrument disclosed in WO 01/91646 A1 is the shape of the staple fastening assembly in which the cartridge device and the anvil have a generally arc-like shape in a cross-sectional plane. This allows for unobstructed view and access towards the concave inner faces of the cartridge device and of the anvil.

When introduced, e.g., into the anal canal, the operational range of the instrument known from WO 01/91646 A1 is restricted, however, and it cannot be used to excise tissue more remote from the rectum because of its limited shaft length.

It is the object of the invention to provide a surgical stapling instrument which has at least two major benefits, i.e. a larger operational range than the stapling instrument disclosed in WO 01/91646 A1 and the ability of being used by gastroenterologists (e.g. GI) in a colonoscopy setting thanks to the possibility to provide the stapling instrument in a size noticeable smaller than the one disclosed in the stapling instrument of WO 01/91646 A1.

This problem is solved by a surgical stapling instrument having the features of claim 1. Advantageous versions of the invention follow from the dependent claims.

The surgical stapling instrument according to the invention comprises, in the distal end region of the instrument, a staple fastening assembly including a curved cartridge device and, opposite to the cartridge device, a curved anvil. The cartridge device comprises at least one curved open row of staples having a concave side and a convex side. The anvil has a staple forming face and is adapted to cooperate with the cartridge device for forming the ends of the staples exiting from the cartridge device. Moreover, a moving device is adapted to move the anvil relatively with respect to the cartridge device, essentially in parallel relationship, from a spaced position for positioning tissue therebetween to a closed position for clamping the tissue. A staple driving device is adapted to drive the staples out of the cartridge device towards the anvil. In the proximal end region of the instrument, a handle is operatively connected to the staple fastening assembly and comprises actuating members coupled to force transmitters of the moving device and of the staple driving device.

Optionally, the stapling instrument includes a knife, which is contained in the cartridge device and which is positioned on the concave side of at least one row of staples and possibly the convex side of at least one row of staples. The knife can be moved towards the anvil by means of a knife actuating device, which is preferably coupled to the staple driving device, e.g. such that, upon actuation of the actuating member of the staple driving device, the staples and the knife advance simultaneously, the knife following the staples such that the tissue is cut after having been stapled.

According to the invention, a flexible backbone is arranged between the handle and the staple fastening assembly. The flexible backbone is a kind of flexible shaft or flexible connection between the handle and the staple fastening assembly and guides the force transmitters of the moving device and of the staple driving device. The flexible backbone can be rather long. It enables the stapling instrument to be introduced, e.g., into the anal canal and to be moved forward for a rather long distance to allow for the treatment of tissue at a site remote from the anus. Upon advancement of the stapling instrument, the flexible backbone adapts to the curvature of the intestine.

In a preferred version of the invention, the flexible backbone comprises a flexible endoscope, which preferably is removably mounted (i.e. it can be detached from the rest of the instrument). The endoscope usually includes observational optics and a light source and optionally comprises a working channel in its longitudinal direction. The working channel can be utilized to place surgical tools at the site of surgery, e.g. an endoscopic gripping instrument for pulling tissue into the space between the cartridge device and the anvil. The application of a flexible endoscope in the backbone of the stapling instrument has the advantage that a standard component is used which can provide flexibility as well as strength to the stapling instrument.

The stapling instrument can be adapted to be used with an independent flexible endoscope forming at least part of the flexible backbone. That means, the stapling instrument according to the invention is distributed without the endoscope, and in order to put it into an operational state, the independently or separately distributed endoscope is connected to the other parts of the instrument. Alternatively, the flexible endoscope is a component or even an integral component of the stapling instrument. These options allow for a large design versatility and cost effectiveness.

In an advantageous version of the invention, the force transmitters of the moving device and of the staple driving device are located at the outside of the endoscope and are attached to the endoscope by a plurality of spaced holders. If the knife actuating device has an independent actuating member at the handle, a force transmitter of the knife actuating device can be arranged at the outside of the endoscope as well. This design uses the endoscope as the only structural connection between the handle and the staple fastening assembly and is particularly simple.

In another version, the flexible backbone comprises a flexible guide, which is arranged alongside the endoscope and which accommodates the force transmitters of the moving device and of the staple driving device. The guide, depending on its design, can connect the handle and the staple fastening assembly in a structural sense.

In a preferred version of the invention, at least one of the force transmitters of the moving device and of the staple driving device comprises a flexible rotary rod adapted to be rotated around its longitudinal axis upon actuation of the related actuating member of the handle and adapted to transform its rotary motion to a longitudinal motion at the staple fastening assembly. The term flexible rod is to be understood in a rather broad sense; it includes, e.g., a tightly wound helix, which is flexible and can transmit torque, and even designs comprising linked members. When force is transmitted from the actuating member at the handle to the staple fastening assembly via a rotary motion, the actual curved shape of the flexible backbone is not affected by this rotary action in which the rotary rod rotates in some guide or sheath. In contrast thereto, a translational movement of force transmitters in a curved flexible shaft tends to straighten the shaft, which would be a great disadvantage in the use of such instrument.

Preferably, at least one of the force transmitters is adapted to be rotated via a gear transmission operated by the related actuating member. Moreover, at least one of the force transmitters can be adapted to transform its rotary motion to a longitudinal motion (required for the relative movement of the anvil with respect to the cartridge device or for expelling the staples) via a screw drive.

The staple forming face of the anvil can be generally planar, but other shapes, e.g. an undulated shape, are conceivable as well.

In an advantageous version of the invention, the staple fastening assembly is adapted to allow unobstructed access towards concave inner faces of the cartridge device and of the anvil. Such design, which is generally known from WO 01/91646 A1, largely facilitates the handling of the stapling instrument in a surgical procedure.

Preferably, the cartridge device and the anvil have a generally arc-like shape in a cross-sectional plane, the arc extending over an angle in the range 10° to 350°.

In a preferred version of the invention, the anvil is supported by means of at least one arm extending from an end of the anvil and generally running in parallel to the direction of relative movement of the anvil with respect to the cartridge device. This arm can be driven by the moving device if the anvil is movable with respect to a fixed cartridge device. An optional second arm, preferably at the other end of the anvil, provides additional strength and facilitates an accurate alignment of the anvil with respect to the cartridge device, which is important for a precise alignment of the ends of the staples with the staple forming face of the anvil. This kind of support allows for a large unobstructed area between the cartridge device and the anvil.

Preferably, the distance between the cartridge device and the anvil in the closed position is adjustable. For example, the moving device can comprise an adjustable stop, e.g. at the related actuating member of the handle, in order to prevent the cartridge device (or anvil) from moving beyond the stop position and from clamping the tissue too much. Or a series of cartridge devices with different built-in tissue stops can be used according to the tissue thickness. It is also conceivable to use a series of cartridge devices which have different longitudinal dimensions which are adapted to the desired distance between the cartridge device and the anvil in the closed position. By adjusting the distance between the cartridge device and the anvil in the closed position, the instrument can be matched to the thickness and type of tissue to be stapled.

In an advantageous version of the surgical stapling instrument, the cartridge device comprises a replaceable cartridge containing the staples. In this way, a used cartridge without staples can be replaced with a fresh one, if required. This is particularly beneficial when the instrument is to be used several times in the same patient.

Preferably, the staple fastening assembly and/or the handle are removably mounted, relative to the flexible backbone, which allows for easier handling and/or partial replacement of the stapling instrument.

Some of the features discussed above are already known from WO 01/91646 A1, in particular an arc-like shape of the cartridge device and the anvil and a support arm extending from an end of the anvil, which enables an easy access to the site of surgery, e.g., for endoscopic optics or additional surgical instruments. Generally, the stapling instrument according to the invention can be used in all kinds of surgery disclosed in WO 01/91646 A1, which is incorporated by reference herein. A particular advantage of the invention, however, is the ability to perform such surgery at locations more remote from an opening in the patient's body and using GI techniques (e.g. non-surgical), such as local anesthesia or sedation.

Herein, the term "staple" is used in a very general sense. It includes metal staples or clips, but also surgical fasteners made of synthetic material and similar fasteners. Synthetic fasteners usually have a counterpart (retainer member) held at the anvil. In this sense, the terms "anvil" and "staple forming face" also have a broad meaning which includes, in the case of two-part synthetic fasteners, the anvil-like tool and its face where the retainer members are held, and similar devices.

DESCRIPTION OF THE DRAWINGS

In the following, the invention is described in more detail by means of embodiments. The drawings show in FIG. 1 an overall isometric view of a first embodiment of the surgical stapling instrument according to the invention, including an endoscope, a staple fastening assembly in the distal end region and a handle in the proximal end region, FIG. 2 an isometric view of the distal portion of the stapling instrument of FIG. 1, FIG. 3 an isometric view of one of several holders spaced along the endoscope, FIG. 4 an isometric view of the internal mechanism of the handle, FIG. 5 a side view of the internal mechanism of the handle, FIG. 6 an isometric view of the distal end of the endoscope, the staple fastening assembly being removed, FIG. 7 an isometric view of the components of the staple fastening assembly driven by the mechanism in the handle, i.e. an arm supporting the anvil and a pusher base used for expelling the staples, FIG. 8 an isometric view similar to FIG. 7, with the staples and a knife added, FIG. 9 an isometric view of some parts of FIG. 8 in a different perspective, FIG. 10 an isometric view of the staple forming face of the anvil and two guide rails used for guiding the knife, FIG. 11 an isometric view of the fully assembled staple fastening assembly with the anvil being in a spaced position, FIG. 12 an isometric view of the staple fastening assembly, a housing being removed, with the anvil being in a closed position and the staples just fired, FIG. 13 an isometric view of parts of FIG. 12 from a different perspective, FIG. 14 an isometric view similar to FIG. 12 with the housing being attached and including the endoscope, FIG. 15 an exploded view of the staple fastening assembly, FIG. 16 an isometric overall view of a second embodiment of the surgical stapling instrument according to the invention, including a flexible guide and an endoscope, and FIG. 17 an isometric view of the distal end region of the embodiment of FIG. 16.

DETAILED DESCRIPTION

Figure 1:
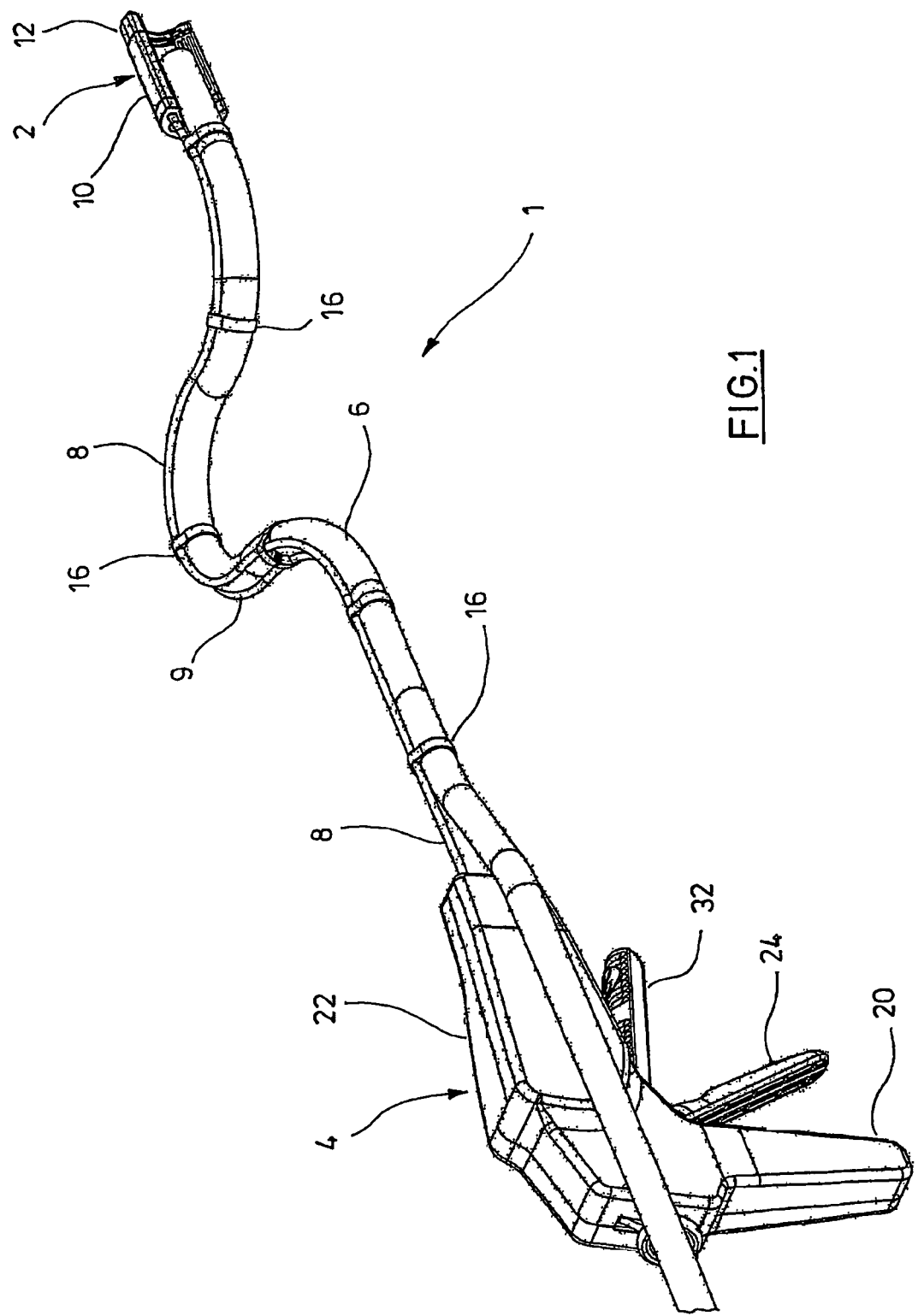

FIG. 1 is an isometric overall view of the surgical stapling instrument 1 according to a first embodiment. The stapling instrument 1 comprises, in its distal end region, a stapling fastening assembly 2 and, in its proximal end region, a handle 4. The handle 4 and the staple fastening assembly 2 are connected via a flexible endoscope 6. In the embodiment, the endoscope 6 is a commercially available endoscope which is not modified in order to be used in the stapling instrument. The endoscope 6 serves as a flexible backbone and provides structural strength.

Figures 2, 3:
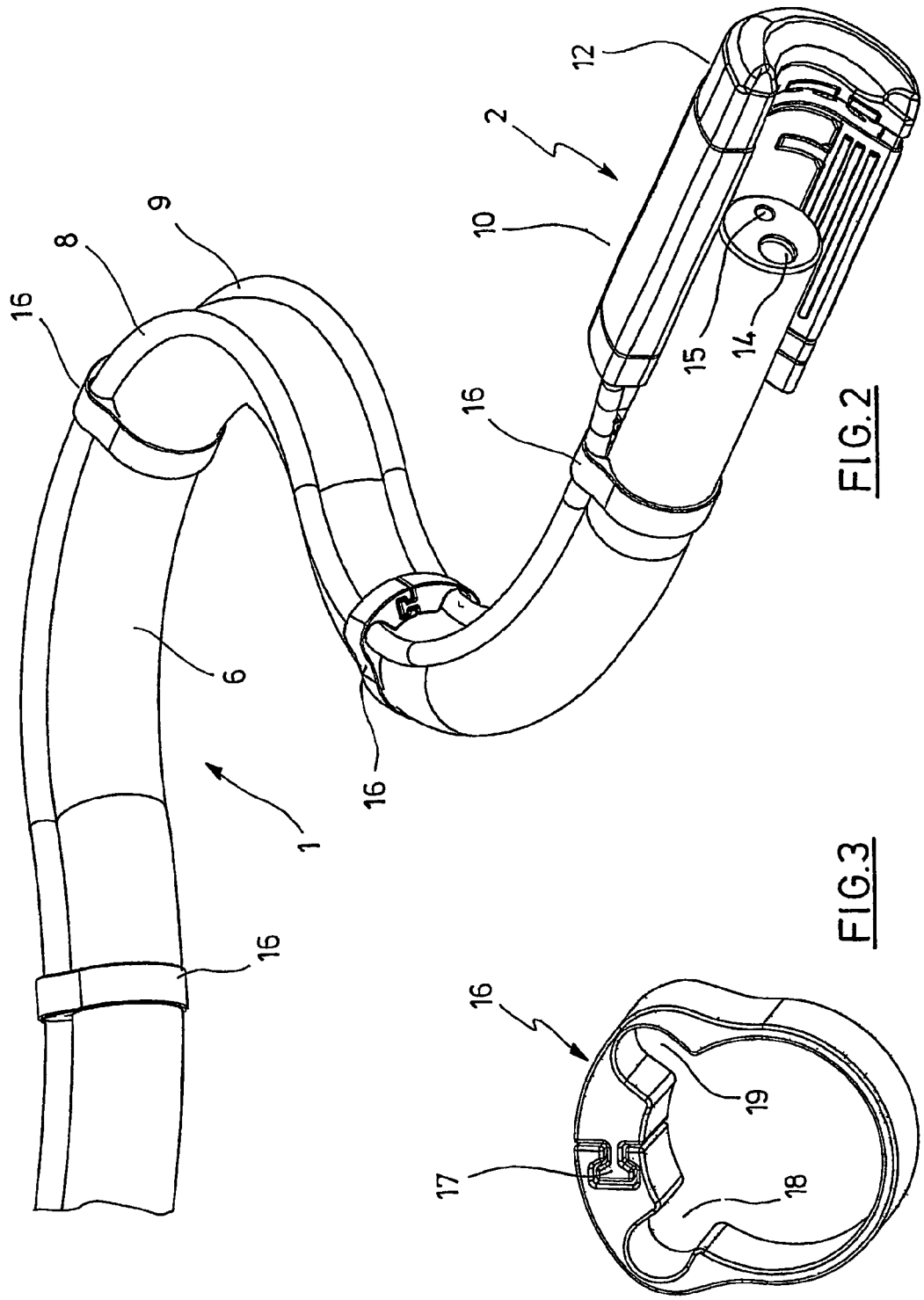

As shown in FIGS. 1 and 2, two force transmitters 8 and 9 running from the handle 4 to the staple fastening assembly 2 are guided by the endoscope 6. The force transmitters are used for transmitting forces from the handle 4 to the staple fastening assembly 2 in order to perform the functions of the stapling instrument 1.

The main components of the staple fastening assembly 2 are a cartridge device 10', which contains several curved open rows of staples as well as a knife, and a curved anvil 12, which has a staple forming face and is adapted to cooperate with the cartridge device for forming the ends of the staples expelled from the cartridge device when stapling instrument 1 is "fired".

The anvil 12 can be moved with respect to the cartridge device 10 in a parallel relationship, i.e. in a direction parallel to the longitudinal axis of the distal end portion of the endoscope 6. In the view of FIG. 2, the anvil 12 has been entirely moved towards the cartridge device 10.

The mechanism and its components of the stapling instrument 1 used for moving anvil 12 relative to cartridge device 10 are generally called moving device, whereas the mechanism and the components used for advancing the staples are generally called staple driving device.

FIG. 2 illustrates that the cartridge device 10 and the anvil 12 have a generally arc-like shape. This design enables an easy access to the working area between cartridge device 10 and anvil 12.

Moreover, FIG. 2 illustrates the arrangement of the distal portion of the endoscope 6 and the staple fastening assembly 2. The distal end face of endoscope 6 has two openings, one for observational optics 14 and one for a light source 15. Optionally, the endoscope can include a working channel which allows the introduction of a surgical instrument having a flexible shaft through the working channel of the endoscope to the site of surgery, i.e. to the area of the staple fastening assembly 2.

In the embodiment, the force transmitters 8 and 9 are attached to the endoscope 6 by means of a plurality of spaced holders 16. FIG. 3 shows one of the holders 16 in enlarged view. Each holder 16 has a lock 17 and two recesses 18 and 19 for accommodating the force transmitters 8 and 9, respectively. For assemblage, the lock 17, which comprises a dovetail-shaped protrusion and a notch fitting thereto, can be opened. The holder 16, which is manufactured from flexible material, allows the insertion of the endoscope 6.

The mechanical connection between the endoscope 6 and the staple fastening assembly 2 or the handle 4 can be entirely accomplished by means of the holders 16 and the force transmitters 8, 9. In particular in the area of handle 4, the flexibility of this design, with no rigid attachment of the handle 4 to the endoscope 6, can be advantageous. In the distal end region of stapling instrument 1, the endoscope 6 may be additionally fixed to the cartridge device 10 of the staple fastening assembly 2, e.g. by bonding.

Figure 4:
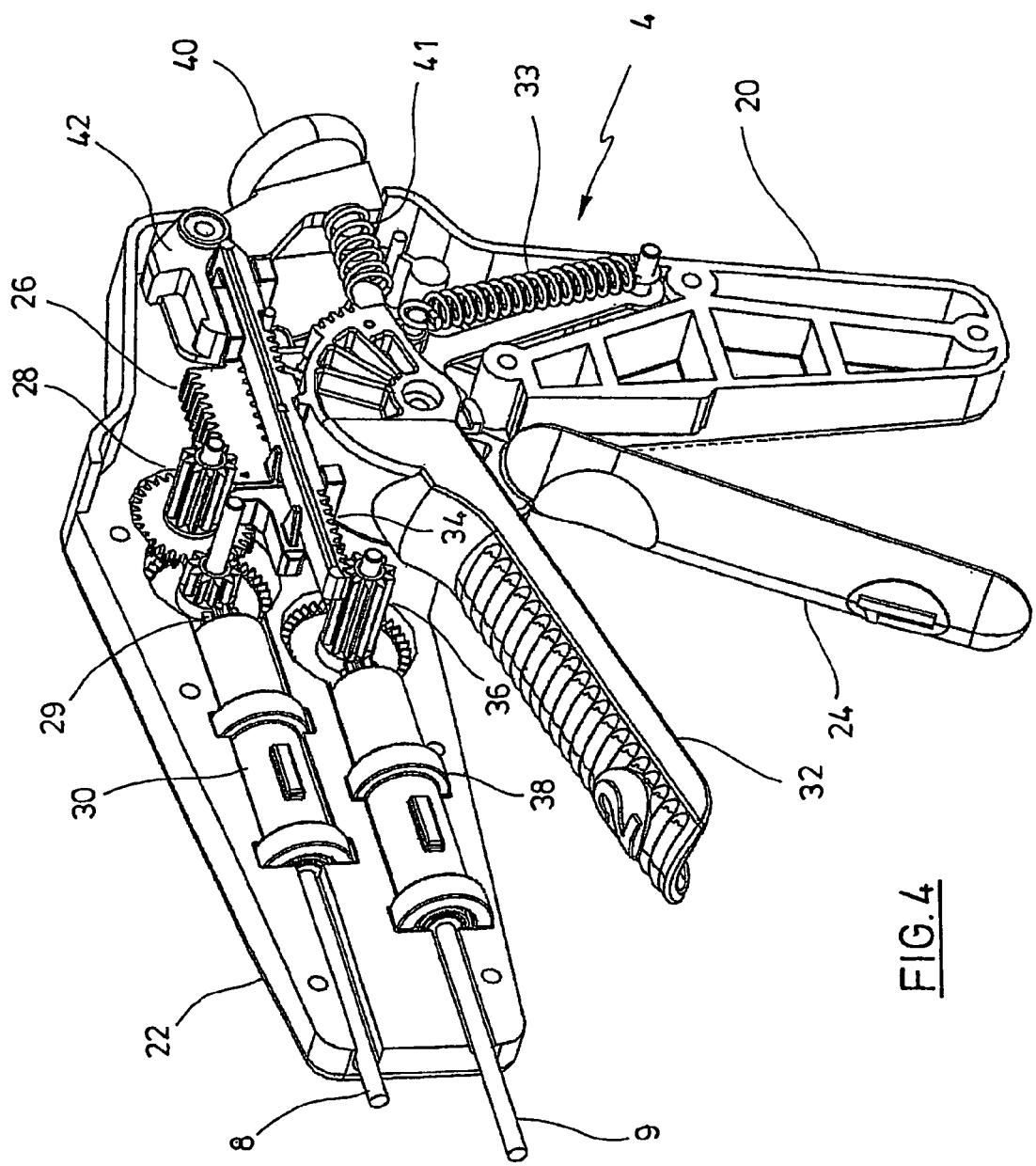
Figure 5:
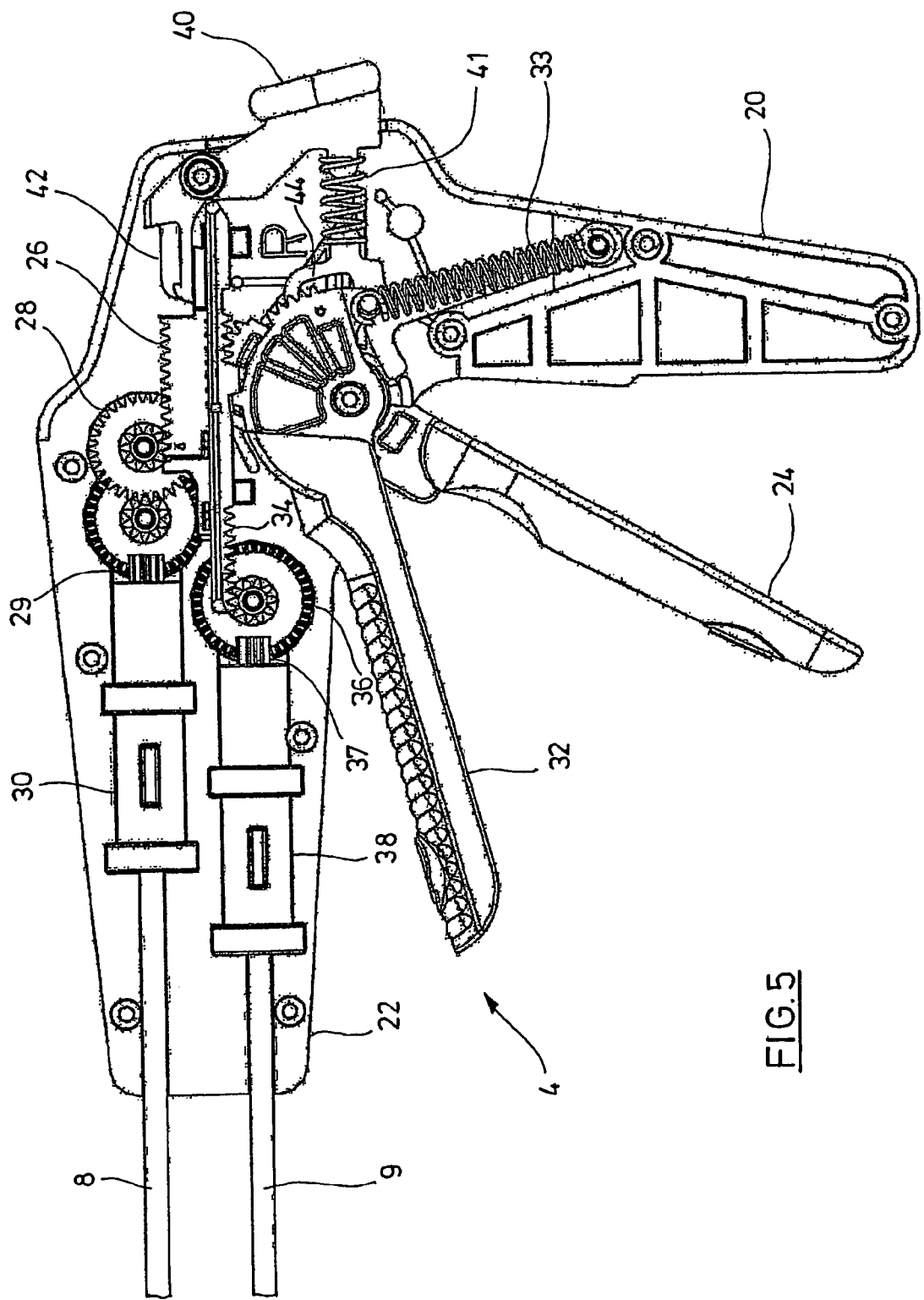

FIGS. 4 and 5 illustrate the internal mechanism of the handle 4. Handle 4 comprises a grip 20 designed to rest in the operator's palm and a gear housing 22.

An actuating member 24 is part of the moving device. When actuating member 24, which is swivellably mounted, is moved towards grip 20, a rack 26 shifts in distal direction and rotates gears 28. The direction of the rotational axis is changed by 90° by means of a pinion 29 at the proximal end of a bearing 30, which supports the proximal end of the force transmitter 8 of the moving device. The force transmitter 8 comprises a rotary rod (see below), the proximal end of which is fixed to pinion 29. Thus, upon pressing the actuating member 24, the rotary rod of the force transmitter 8 is caused to a rotary movement about a longitudinal axis. Because of the gear ratio provided by gears 28 and pinion 29, this rotational movement is relatively fast.

In a similar way, upon pressing a swivellably mounted actuating member 32 against the force of a spring 33 ("firing" the instrument), a rack 34 shifts in distal direction and drives gears 36 and a pinion 37 at the proximal end of a bearing 38, which results in a relatively fast rotational movement of a rotary rod of the force transmitter 9 of the staple driving device.

In order to release (retract) the staple driving device after the staples have been "fired", a release button 40 has to be pressed against the force exerted by a spring 41. After "firing" and before pressing release button 40, a catch 42 engages to a protrusion of the staple driving device and keeps rack 34 in a distal position. Moreover, rack 26 is held forward and in place by this mechanism as well, while actuating member 32 is pressed. Pressing release button 40 lifts the catch 42, which releases the protrusion of the staple driving device such that, via the action of spring 33, rack 34 returns to its original proximal position.

A safety feature (not shown in detail) is a pin held by a part 44 until part 44 is pushed out of the way upon actuation of actuating member 24. This ensures that actuating member 32 cannot be used prior to actuating member 24.

Figure 6:
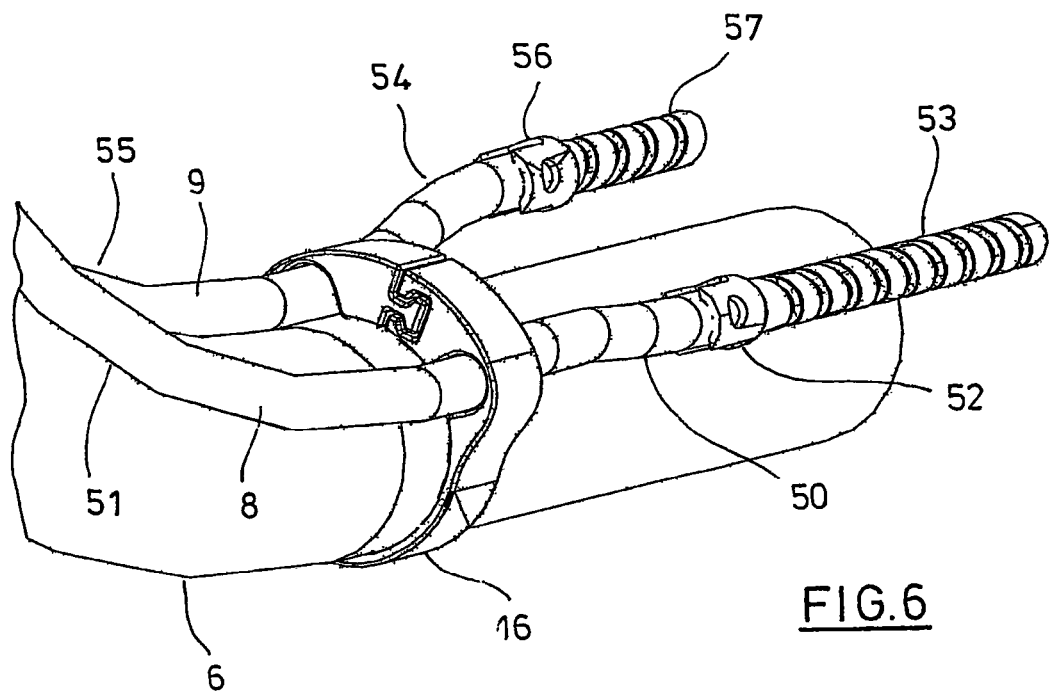

FIG. 6 shows the distal end region of the force transmitters 8 of the moving device and 9 of the staple driving device, including the most distal holder 16 and the distal end area of endoscope 6.

Force transmitter 8 comprises a flexible rotary rod 50 which is rotatably mounted in a flexible sheath 51. In the embodiment, rotary rod 50 is a single flexible structure all along. Different designs, e.g. a structure comprising flexibly linked short rigid members or a tightly wound helix, are conceivable as well. At its distal end, rotary rod 50 is fixed to a connector 52 which is attached to the proximal end of a drive screw 53. In a similar way, force transmitter 9 includes a rotary rod 54, which is guided in a sheath 55 and ends at a connector 56 fixed to a drive screw 57.

Figure 7:
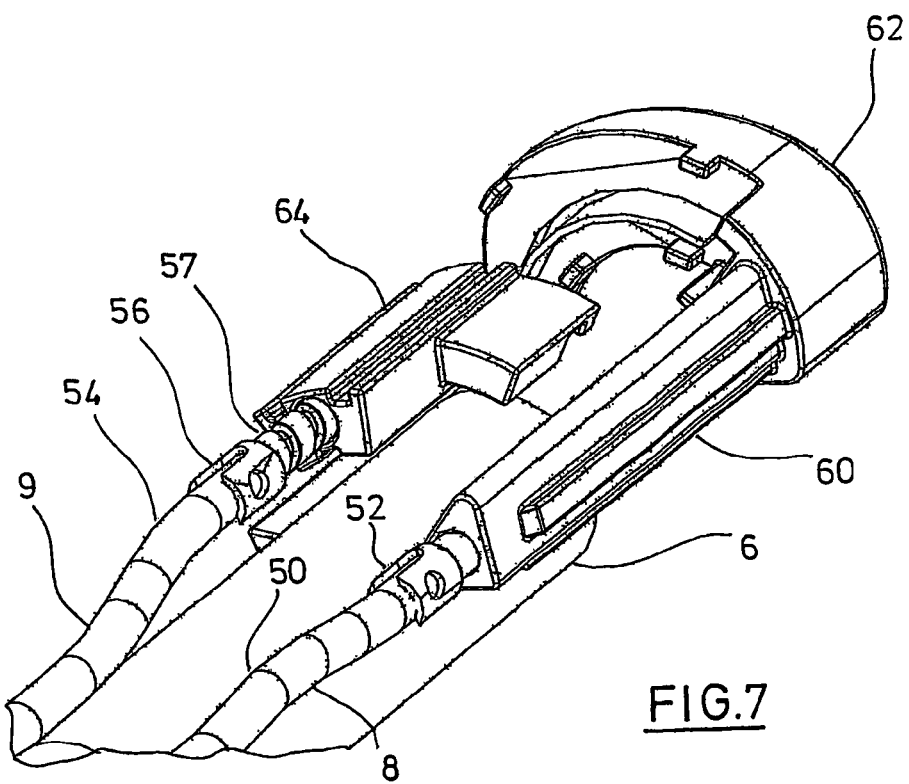

FIG. 7 displays the components driven by the screws 53 and 57, but not yet the guiding parts or rails for these components. Screw 53 fits into a threaded hole extending into longitudinal direction inside an arm 60 which supports an anvil housing 62. Similarly, screw 57 fits into a threaded hole in a pusher base 64. Thus, by rotating rotary rods 50 or 54, the arm 60 and the pusher base 64, respectively, are moved in longitudinal direction of the staple fastening assembly 2.

Figure 8:
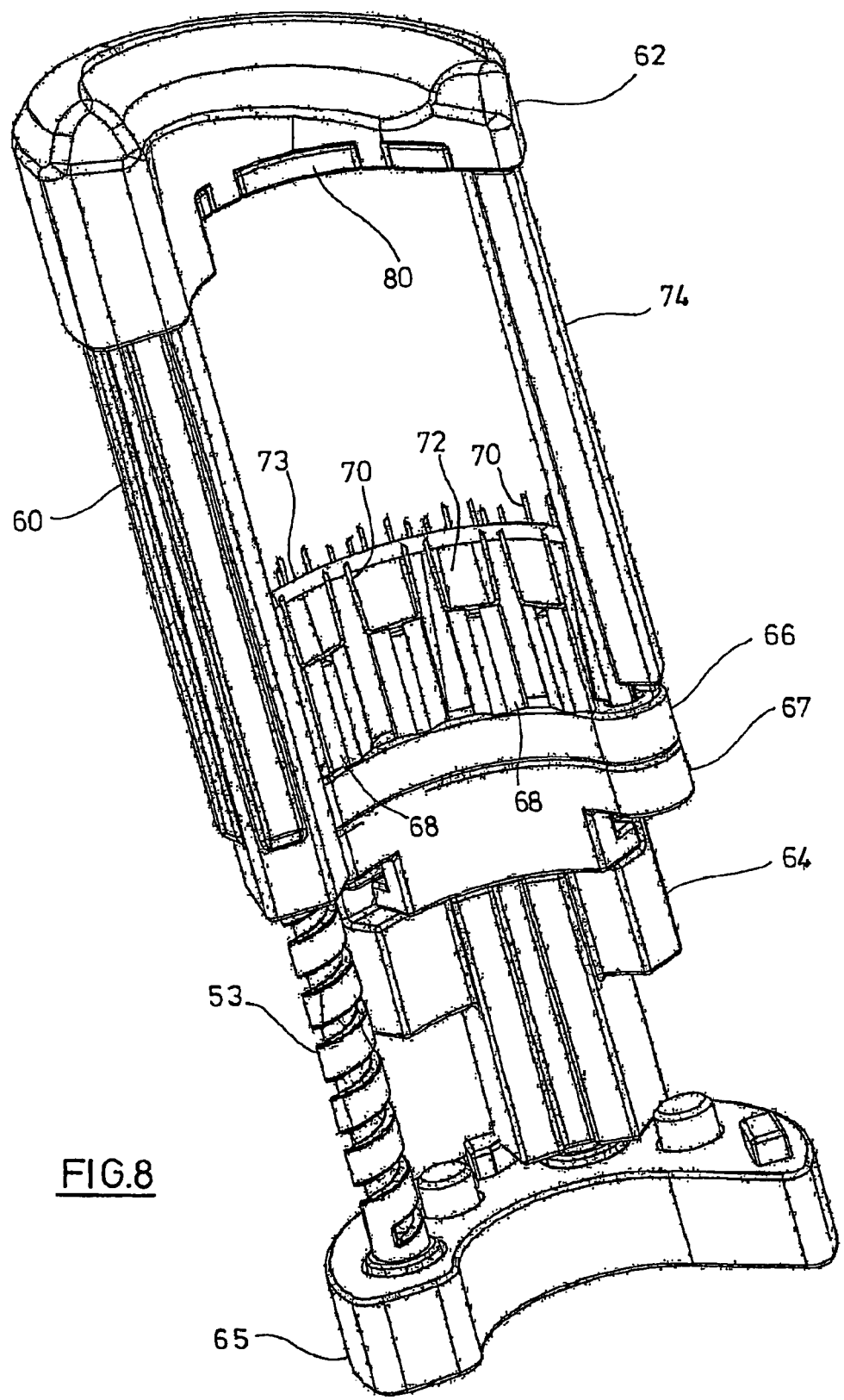

FIG. 8 shows additional components of the staple fastening assembly 2. Both screws 53 and 57 are guided by bores in an arcuate base 65 of the staple fastening assembly 2. Pusher base 64 supports (via an intermediate part 67) a pusher platform 66 from which a plurality of pusher fingers 68 extend longitudinally. Each of the pusher fingers 68 supports a staple 70 such that the pointed ends of the staples 70 are aligned in distal direction. The pusher fingers 68 and the related staples 70 are guided in individual slots (not shown in FIG. 8) formed in the housing of the cartridge device 10. Moreover, the intermediate part 67 supports an arcuate knife 72 having a concave side (seen in FIG. 8), a convex side opposite to the concave side and a cutting edge 73. FIG. 8 also shows a guide arm 74 of the anvil 12 which extends from the anvil housing 62 and runs in parallel to arm 60.

Figure 9:
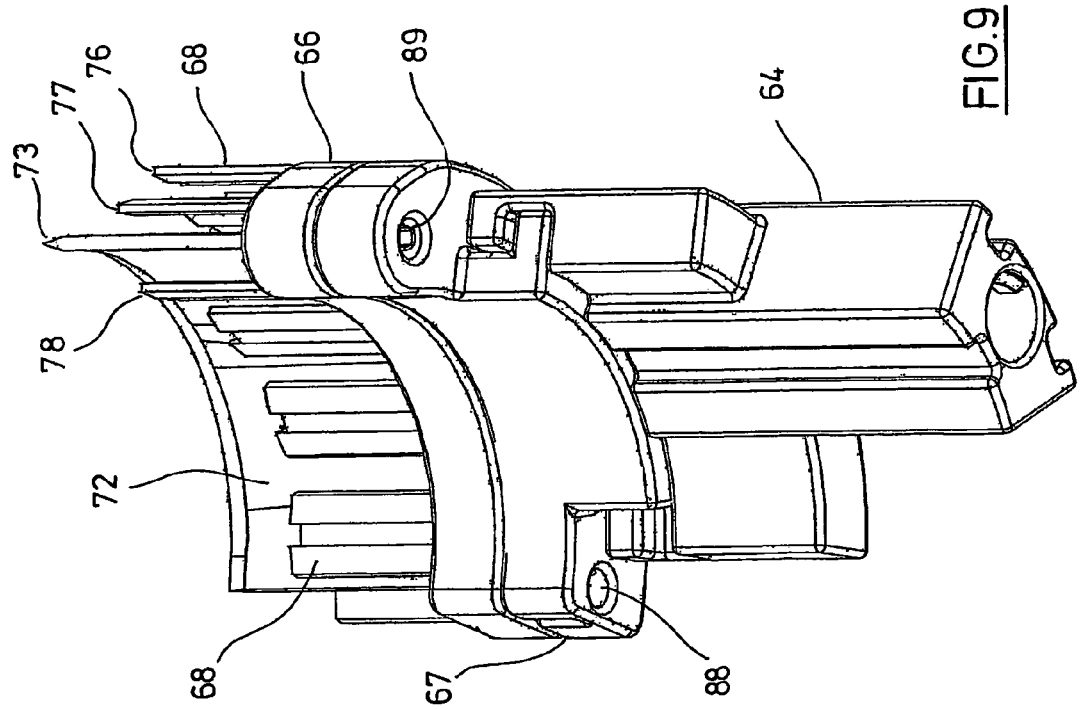

FIG. 9 provides a better impression of the arrangement of the staples 70 (which are not shown in FIG. 9 but indicated by the locations of the pusher fingers 68) and the knife 72.

The cartridge device 10 comprises three curved open rows of staples, i.e. two rows 76 and 77 on the convex side of knife 72 and one row 78 on the concave side of knife 72.

Figure 10:
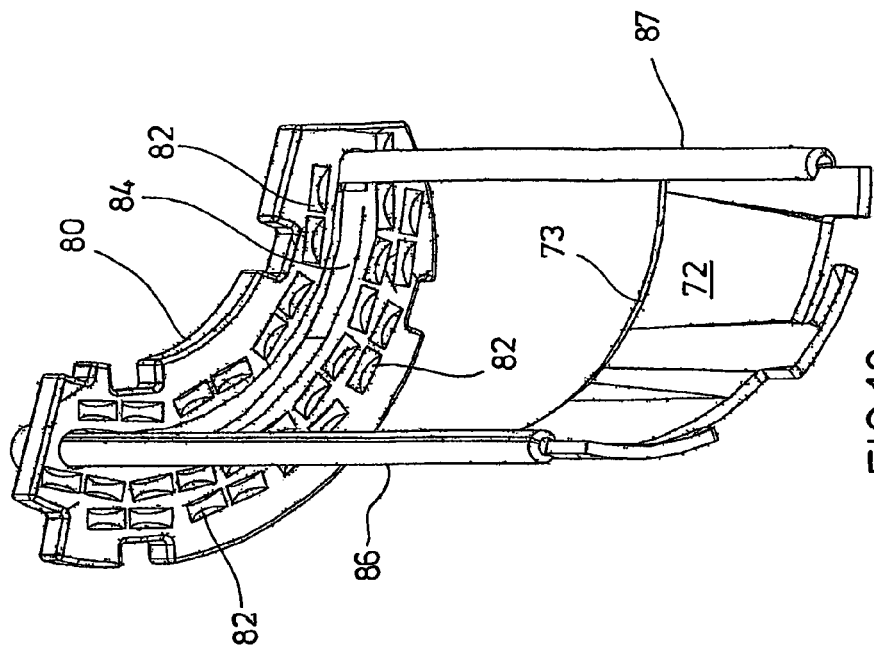

A staple forming face 80, which is mounted on the anvil housing 62 (see FIG. 8), is shown in FIG. 10. The staple forming face 80 is preferably made of metal and comprises three rows of staple forming depression 82, which are aligned to the pointed ends of staples 70. Moreover, FIG. 10 displays a knife depression 84, which is aligned to the cutting edge 73 of knife 72 and preferably filled with a plastics material which acts as cutting block but can be cut by the knife 72.

Fixed to the staple forming face 80, there are two guide rails 86 and 87 which have a lateral slot each for precisely guiding the knife 72, even when it is very close to the staple forming face 80, as illustrated in FIG. 10. When the anvil 12 is moved with respect to the cartridge device 10 by means of the moving device, the guide rails 86 and 87 move in longitudinal direction as well and slide through holes 88 and 89 (see FIG. 9) provided in the intermediate part 67 and the pusher platform 66. This movement does not affect the position of the knife 72, because knife 72 is fixed to the intermediate part 67.

Figure 11:
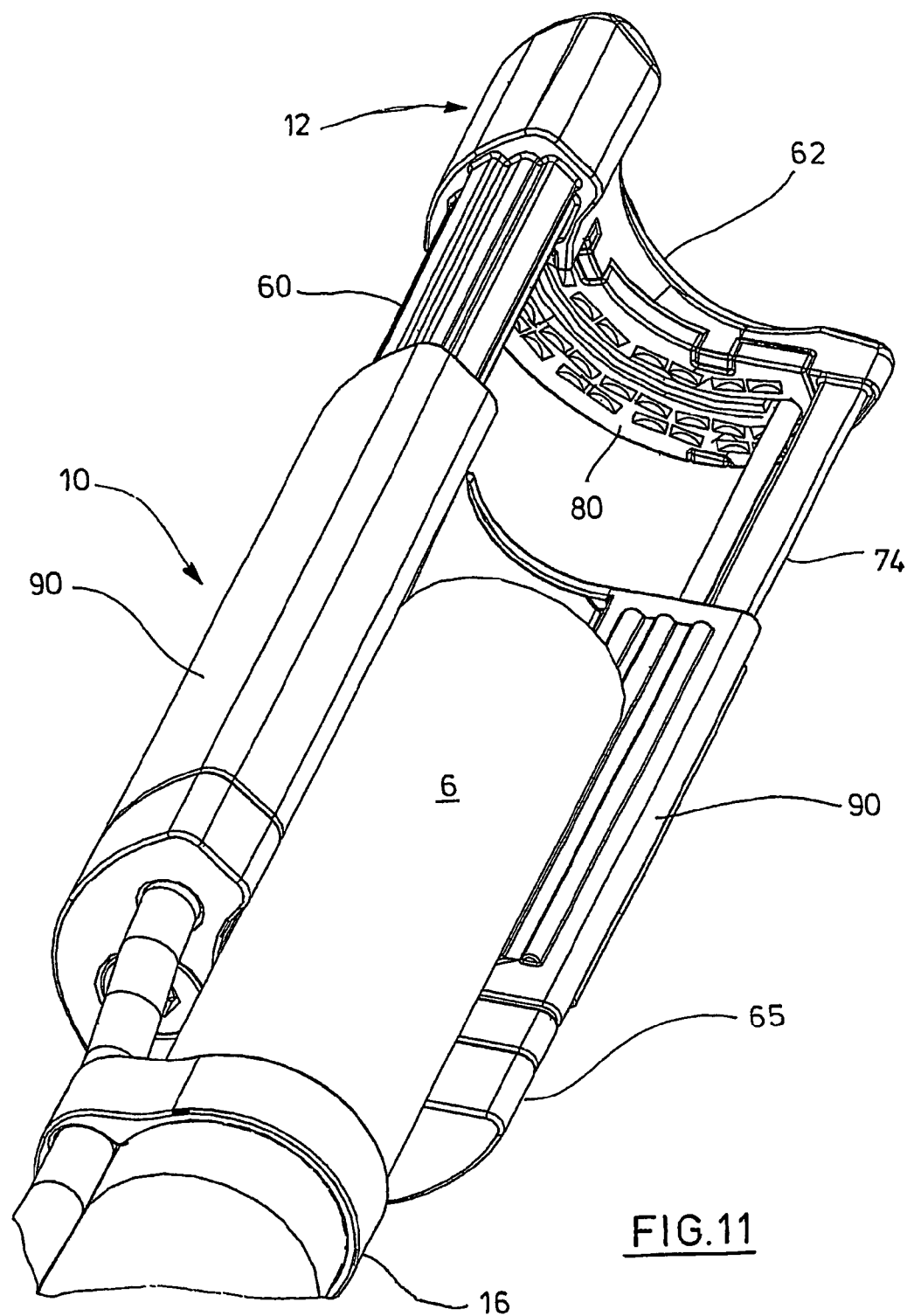

FIG. 11 is a view similar to FIG. 8, but the cartridge device 10 has been completed by a housing 90. In the embodiment, the housing 90 is an injection-molded part made of medical grade plastics material.

FIG. 11 illustrates the state in which the anvil 12 has been moved to a spaced position, i.e. to a position in which the distance between the cartridge device 10 and the staple forming face 80 of the anvil 12 is large. This corresponds to a large exposed area of drive screw 53 in FIG. 8. In this spaced position, tissue of a patient to be excised can be pulled between the staple forming face 80 of anvil 12 and the cartridge device 10. Thereafter, actuating member 24 of the moving device is pressed towards grip 20, which causes a rotational movement of rotary rod 50 and drive screw 53, resulting in a shift of the anvil 12 in proximal direction. In this way, the anvil 12 reaches a closed position and the tissue is clamped.

Figure 12:
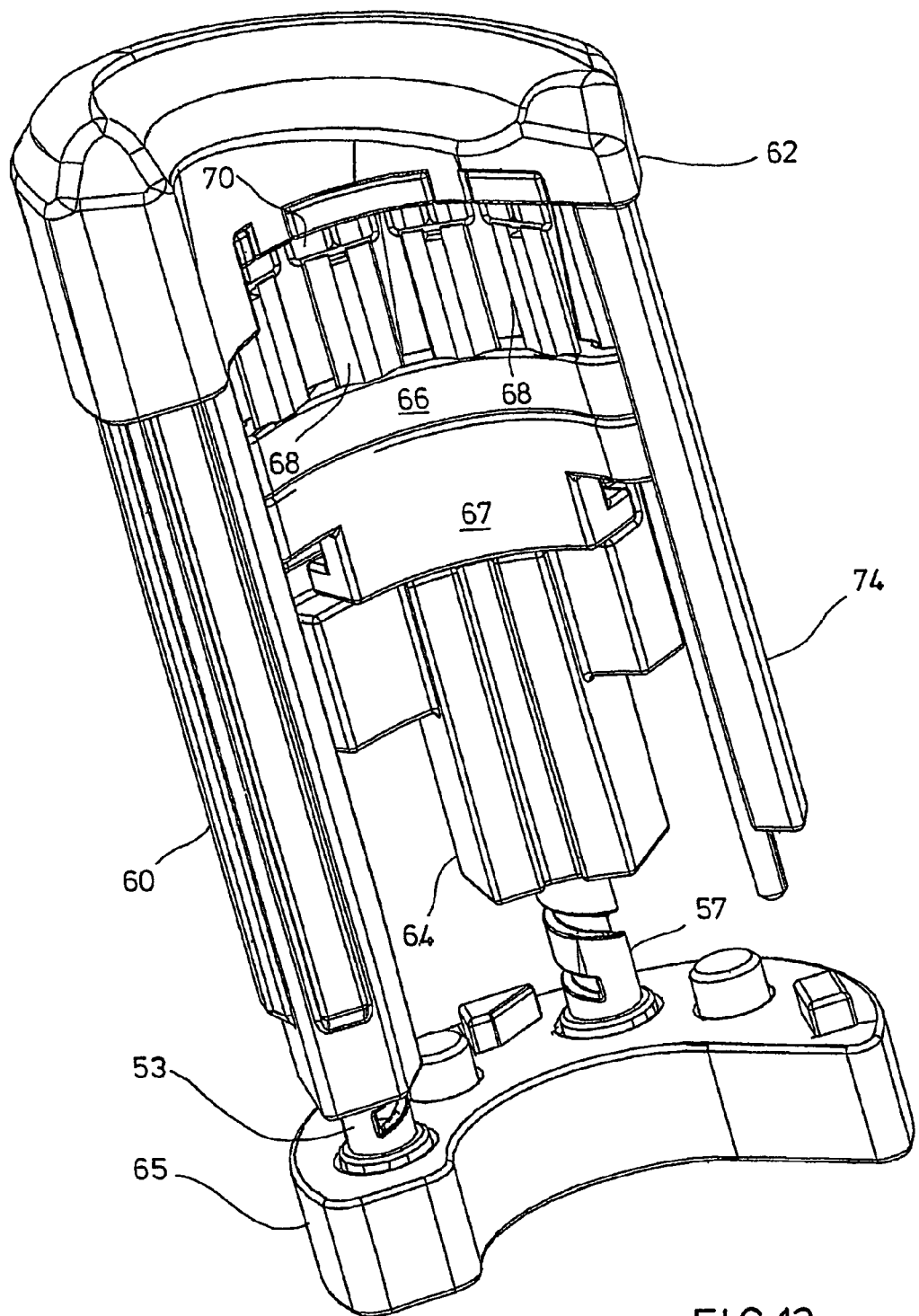

The next step of the procedure is shown in FIG. 12 (in which the housing 90 is removed). As explained, the anvil 12 has been moved to a closed position, which is evident from a small exposed area of drive screw 53. Moreover, actuating member 32 has been pressed, which results in a rotational movement of screw 57 and a longitudinal movement in distal direction of the pusher base 64, the intermediate part 67, the pusher platform 66, the pusher fingers 68, the staples 70 and the knife 72, wherein the cutting edge 73 of knife 72 follows the pointed ends of the staples 70.

FIG. 12 shows the state when the staples 70 have been formed by staple forming face 80. FIG. 13 displays the same state. FIG. 14 shows a complete view of the cartridge device 10, the anvil 12 and the distal end region of endoscope 6 in the same state. After the tissue has been stapled, it is cut and excised by the knife 72. In this way, the tissue to stay with the patient is safely stapled by the rows 76 and 77 of staples on the convex side of knife 72, which immediately stops bleeding, whereas the part of the tissue to be removed from the patient is stapled and held together by the staples of row 78. After stapling, release button 40 is pressed, such that rack 34 and actuating member 32, by means of the force exerted by spring 33, return to their original positions. Additionally, this effects a reverse motion of the moving device, increasing the distance between the anvil 12 and the cartridge device 10 in order to release the clamped tissue and to be able to remove the stapling instrument 1 from the patient. The excised portion of the tissue remains in the staple fastening assembly 2.

Figure 15:
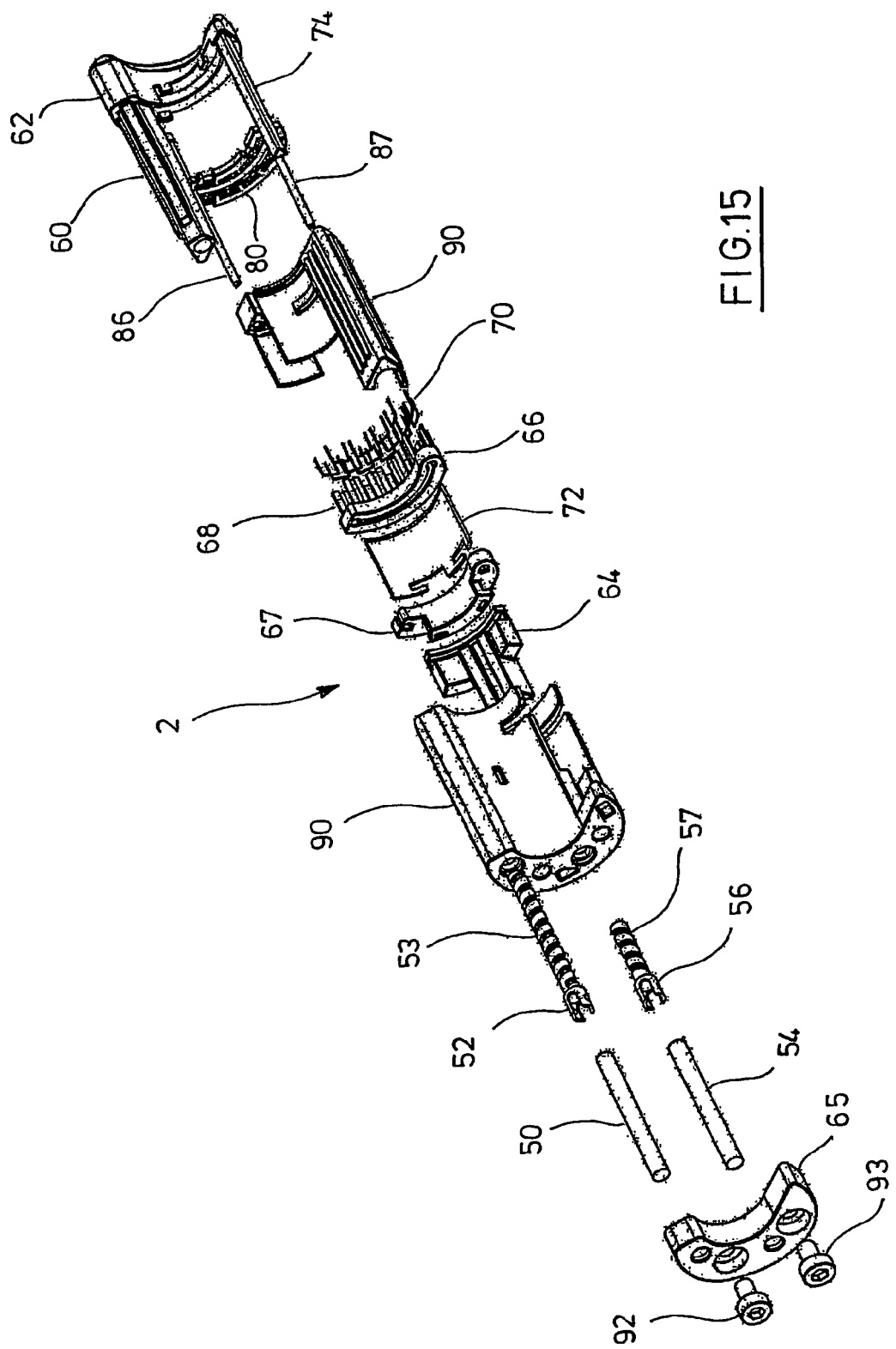

FIG. 15 illustrates the components of the staple fastening assembly 2 of the embodiment described so far in an exploded view. Screws 92 and 93 are used to attach the arcuate base 65 to part of the housing 90 of cartridge device 10.

Figure 16:
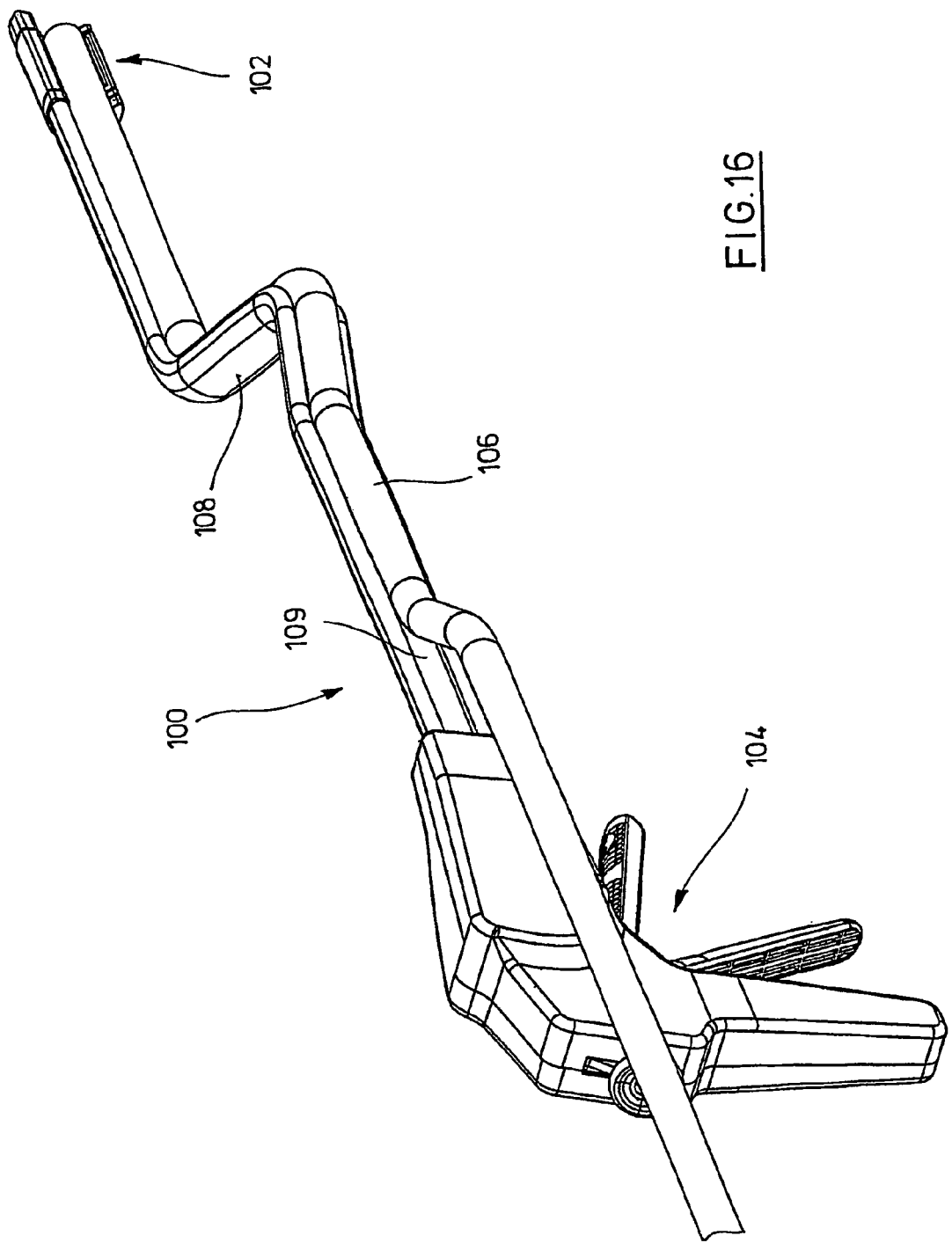
Figure 17:
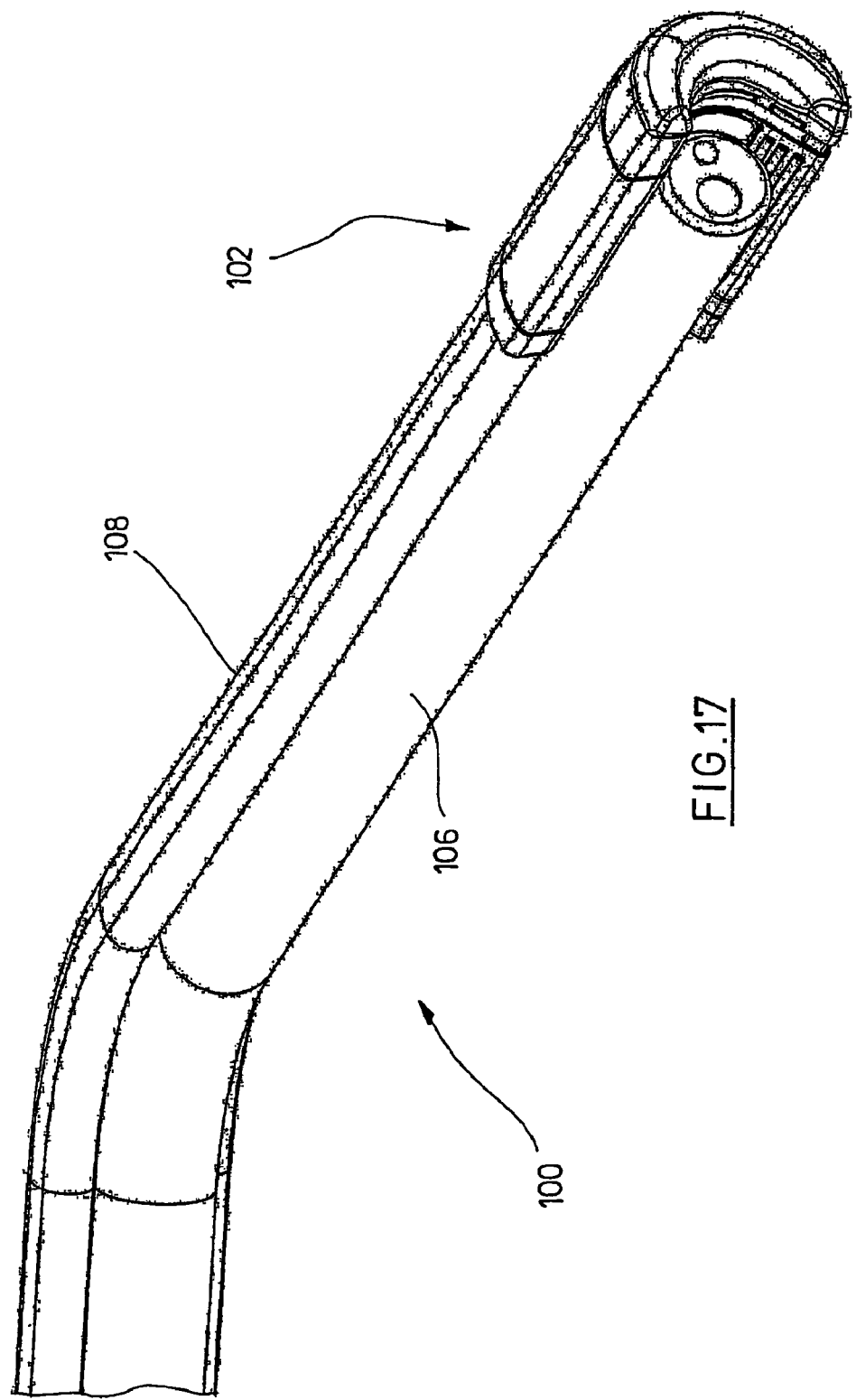

FIGS. 16 and 17 display a second embodiment of the surgical stapling instrument, i.e. the stapling instrument 100. Its staple fastening assembly 102 and its handle 104 have a similar design as the staple fastening assembly 2 and the handle 4 of the first embodiment. In contrast thereto, however, the force transmitters are not exposed at the outer periphery of endoscope 106, but are accommodated in a flexible guide 108. The endoscope 106 and the flexible guide 108 form the flexible backbone of stapling instrument 100.

In the embodiment, the flexible guide 108 is made of plastics material and comprises two longitudinal channels for guiding rotary rods of the force transmitters of the moving device and of the staple driving device. An open channel 109 longitudinally extends alongside flexible guide 108. The endoscope 106 can rest within open channel 109, as shown in FIGS. 16 and 17.

The function and use of the stapling instrument 100 are the same as those of stapling instrument 1.

The invention claimed is:
1. A Surgical stapling instrument comprising:
  a staple fastening assembly in a distal end region of the instrument, including a curved cartridge device, which comprises at least one curved open row of staples having a concave side and a convex side, and, opposite to the cartridge device, a curved anvil, which has a staple forming face and is adapted to cooperate with the cartridge device for forming the ends of the staples exiting from the cartridge device;
  a moving device adapted to move the anvil relatively with respect to the cartridge device, essentially in parallel relationship, from a spaced position for positioning tissue therebetween to a closed position for clamping the tissue;

a staple driving device adapted to drive the staples out of the cartridge device towards the anvil;

a handle in a proximal end region of the instrument, the handle is operatively connected to the staple fastening assembly and comprises actuating members coupled to force transmitters of the moving device and of the staple driving device; and a flexible backbone arranged between the handle and the staple fastening assembly, the flexible backbone guides the force transmitters of the moving device and of the staple driving device; and wherein the force transmitters of the moving device and of the staple driving device are located at the outside of the flexible backbone.

2. The stapling instrument according to claim 1, further including:

a knife which is contained in the cartridge device and which is positioned on the concave side of at least one row of staples; and a knife actuating device adapted to move the knife towards the anvil, which knife actuating device preferably is coupled to the staple driving device.

3. The stapling instrument according to claim 1, wherein the flexible backbone comprises a flexible endoscope, which preferably is removably mounted.

4. The stapling instrument according to claim 3, wherein the force transmitters of the moving device and of the staple driving device are located at the outside of the endoscope and are attached to the endoscope by a plurality of spaced holders.

5. The stapling instrument according to claim 3, wherein the flexible backbone comprises a flexible guide which is arranged alongside the endoscope and which accommodates the force transmitters of the moving device and of the staple driving device.

6. The stapling instrument according to claim 1, wherein the stapling instrument is adapted to be used with an independent flexible endoscope forming at least part of the flexible backbone.

7. The stapling instrument according to claim 1, wherein at least one of the force transmitters of the moving device and of the staple driving device comprises a flexible rotary rod adapted to be rotated around its longitudinal axis upon actuation of the related actuating member of the handle and adapted to transform its rotary motion to a longitudinal motion at the staple fastening assembly.

8. The stapling instrument according to claim 7, wherein the at least one of the force transmitters is adapted to be rotated via a gear transmission operated by the related actuating member.

9. The stapling instrument according to claim 7, wherein the at least one of the force transmitters is adapted to transform its rotary motion to a longitudinal motion via a screw drive.

10. The stapling instrument according to claim 9, wherein the staple fastening assembly (2) is adapted to allow unobstructed access towards concave inner faces of the cartridge device (10) and of the anvil (12).

11. The stapling instrument according to claim 10, wherein the staple forming face of the anvil is generally planar.

12. The stapling instrument according to claim 11, wherein the cartridge device and the anvil have a generally arc-like shape in a cross-sectional plane, the arc extending over an angle in the range 10° to 350°.

13. The stapling instrument according to claim 12, wherein the anvil is supported by means of at least one arm (60, 74) extending from an end of the anvil and generally running in parallel to the direction of relative movement of the anvil with respect to the cartridge device (10).

14. The stapling instrument according to claim 13, wherein the distance between the cartridge device and the anvil in the closed position is adjustable.

15. The stapling instrument according to claim 14, wherein the cartridge device comprises a replaceable cartridge containing the staples.

16. The stapling instrument according to claim 15, wherein the staple fastening assembly is removably mounted.

17. Stapling instrument according to claim 16, wherein the handle is removably mounted.

* * * * *